United States Patent
Bishop

[11] Patent Number: 5,881,781
[45] Date of Patent: Mar. 16, 1999

[54] PIPETTING STATION FOR SAMPLE TESTING MACHINE

[75] Inventor: James Clement Bishop, Columbia, Mo.

[73] Assignee: bioMerieux Vitek, Inc., Hazelwood, Mo.

[21] Appl. No.: 799,475

[22] Filed: Feb. 12, 1997

Related U.S. Application Data

[62] Division of Ser. No. 604,461, Feb. 21, 1996.

[51] Int. Cl.[6] ....................................... B65B 1/04
[52] U.S. Cl. ...................... 141/284; 141/130; 221/203; 436/54
[58] Field of Search .................. 141/65, 67, 98, 141/130, 387, 284, 248; 221/200, 203, 210, 298; 422/100; 436/49, 54; 73/864.14, 863.32

[56] References Cited

U.S. PATENT DOCUMENTS

| | | | |
|---|---|---|---|
| 3,475,127 | 10/1969 | Gilford | 23/230 |
| 3,567,398 | 3/1971 | Farr | 23/259 |
| 3,712,794 | 1/1973 | Farr | 23/259 |
| 3,737,072 | 6/1973 | Deitrick | 221/203 |
| 3,834,839 | 9/1974 | Krebs et al. | 417/505 |
| 3,851,530 | 12/1974 | Symonds et al. | 73/395 |
| 4,037,760 | 7/1977 | Hirschfeld | 222/145 |
| 4,244,919 | 1/1981 | Chen | 422/100 |
| 4,265,855 | 5/1981 | Mandle et al. | 422/65 |
| 4,270,670 | 6/1981 | Christiani et al. | 221/211 |
| 4,274,194 | 6/1981 | Rizzo | 29/717 |
| 4,555,957 | 12/1985 | Frankel et al. | 73/864.14 |
| 4,567,997 | 2/1986 | Portyansky | 221/233 |
| 4,656,007 | 4/1987 | Douchy et al. | 422/64 |
| 4,684,045 | 8/1987 | Su | 222/456 |
| 4,790,451 | 12/1988 | Cassou et al. | 221/233 |
| 4,863,695 | 9/1989 | Fullemann | 422/100 |
| 4,877,585 | 10/1989 | Perlman | 422/100 |
| 5,008,082 | 4/1991 | Shaw | 422/65 |
| 5,063,790 | 11/1991 | Freeman et al. | 73/864.14 |
| 5,100,021 | 3/1992 | Mussi | 221/155 |
| 5,192,506 | 3/1993 | Kureshy . | |
| 5,200,151 | 4/1993 | Long . | |
| 5,213,761 | 5/1993 | Sakagami | 436/54 |
| 5,213,764 | 5/1993 | Kerr et al. | 436/54 |
| 5,260,030 | 11/1993 | DeVaughn . | |
| 5,265,398 | 11/1993 | VanAlstine et al. . | |
| 5,270,219 | 12/1993 | DeCastro et al. . | |
| 5,298,425 | 3/1994 | Kuhn et al. . | |
| 5,343,909 | 9/1994 | Goodman . | |
| 5,372,782 | 12/1994 | Karkantis et al. . | |
| 5,374,395 | 12/1994 | Robinson et al. . | |
| 5,378,630 | 1/1995 | Kai et al. . | |
| 5,384,095 | 1/1995 | Golz et al. . | |
| 5,391,499 | 2/1995 | Karkantis et al. . | |
| 5,415,840 | 5/1995 | Sano et al. . | |

*Primary Examiner*—J. Casimer Jacyna
*Assistant Examiner*—Steven O. Douglas
*Attorney, Agent, or Firm*—McDonnell Boehnen Hulbert & Berghoff

[57] ABSTRACT

A diluting station and a pipetting station for a machine such as a biological sample testing machine. The diluting station has a rotating shot tube that fills with diluent without the need for priming when the shot tube is in a vertically inclined orientation, and which dispenses the diluent into a receptacle when the shot tube is rotated to a downward orientation. A thimble valve is placed in the shot tube to control the flow of diluent into the valve.

The pipetting station includes a cylindrical housing storing a plurality of straws and a concentric rotating drum that sweeps a straw into a straw withdrawal slot. A tubular tapered transfer pin is inserted into frictional engagement with the straw. The tubular transfer pin rotates the straw out of the slot and into a generally downward orientation towards a receptacle containing a fluid. The pin and straw are lowered so as to place the end of the straw into the fluid. The fluid is withdrawn into the straw by means of vacuum applied to the tubular tapered transfer pin. The pin and straw are then raised out of the fluid. The fluid can then be deposited into a second receptacle that is moved below the straw and transfer pin by lowering the straw into the second receptacle and releasing the vacuum.

12 Claims, 11 Drawing Sheets

PIPETTING STATION FOR SAMPLE TESTING MACHINE

This is a divisional of application Ser. No. 08/604,461, filed Feb. 21, 1996, pending.

BACKGROUND OF THE INVENTION

A. Field of the Invention

This invention generally relates to the field of methods and devices for adding, removing and transferring precise volumes of fluid to and/or from a receptacle such as a test tube. These methods and devices are often employed in biological and fluid sample testing machines and related equipment.

The dilution station of the present invention is suitable for use in machines in which a precise volume of fluid (such as a diluent solution or reagent solution) is automatically added to a receptacle for the fluid. The pipetting station is suitable for use in machines which have the need for automatic and accurate removal of a predetermined volume of fluid from a receptacle. While the invention is particularly suitable to automated biological sample testing machines, it is also applicable to other types of machines, as will be more fully understood from the following discussion.

B. Description of Related Art

Automated biological sample testing equipment typically involve the processing of biological samples by multiple modules or "stations", with each station designed to perform a particular function. For example, in the medical area, biological samples are placed in test tubes and processed according to a predetermined methodology.

One common step in the processing of biological samples is the step of adding a fluid to a sample, such as diluting a sample with a diluent, for example, water or saline solution. Prior art techniques for diluting a sample are described in the patents to Douchy et al., U.S. Pat. No. 4,656,007 and Chen, U.S. Pat. No. 4,244,919, and the early patents to Farr, U.S. Pat. Nos. 3,712,754 and 3,567,398.

Another step sometimes found in the processing of biological samples is the removal of fluids from a sample, and the transferring of the removed fluid to another site or receptacle. Representative techniques for handling or removing fluid samples are described in U.S. Pat. No. 4,265,855 to Mandle et al., and the patents to Freeman, U.S. Pat. No. 5,063,790 and Goodman, U.S. Pat. No. 5,343,909.

When samples are to be removed from one receptacle and transferred to another, special problems are encountered. If a pipetting device is used for the removal of fluid, the pipette must be disposed of and a new pipette supplied to the device to avoid contamination between samples. Several patents addressing the challenges of dispensing or handling pipettes and other similarly shaped objects include the patent to Prussi, U.S. Pat. No. 5,100,021, which discloses a package for manual removal of pipettes, and the patents to VanAlstine et al., U.S. Pat. No. 5,265,398; Portyansky, U.S. Pat. No. 4,567,997; Rizzo, U.S. Pat. No. 4,274,194 and Cristiani et al., U.S. Pat. No. 4,270,670.

The present invention overcomes the limitations of the prior art approaches by providing for an efficient and compact arrangement for diluting and pipetting stations. The diluting station provides for precise control of the amount of diluent added to the receptacle, and does not require priming of the diluent addition vessel. The diluting station accomplishes automatic addition of the diluent to the receptacle with a negligible risk of contamination of the diluent or of the diluting apparatus. The pipetting station is particularly advantageous in that it permits disposable straws to be used in the removal of fluids from a sample. The pipetting station achieves the withdrawal of the straws from a hopper and removal of fluid from the receptacle automatically and without human intervention. The pipetting station also accomplishes automatic disposal of the straws after the removed fluid has been transferred to another body, such as to a second receptacle.

SUMMARY OF THE INVENTION

A diluting station is provided for dispensing a controlled volume of fluid into a receptacle, comprising a source of fluid, a shot tube comprising a tip portion, a hollow body, and a fluid port, and a conduit for conducting the fluid from the source to the fluid port. A means is provided for rotating the shot tube from a first position, wherein the tip portion is oriented at an incline above horizontal relative to the hollow body during filling of the shot tube, to a second position, wherein the tip portion is oriented downward towards the receptacle during dispensing of the fluid. A valve is provided for controlling the flow of the fluid into the shot tube. By virtue of the upward orientation of the shot tube during filling, air within the shot tube is eliminated from the shot tube during the filling process, eliminating the need for priming the shot tube.

Preferably, the source of fluid comprises a reservoir of fluid placed above the shot tube, whereby the fluid fills the shot tube by gravity flow of the fluid. An exhaust port is preferably provided in the shot tube, and a conduit links the exhaust port to a source of compressed air. When the shot tube is rotated to said second position, the source of compressed air delivers a stream of air to the interior of the shot tube, exhausting the fluid from the shot tube.

The pipetting station includes a straw hopper or housing containing a plurality of hollow straws and defining a straw withdrawal opening. A tapered, tubular transfer pin having a tip portion is positioned adjacent to the housing. A source of vacuum is connected to the transfer pin. A drive mechanism for the transfer pin is provided to move the transfer pin into and out of engagement with a straw placed or located in the straw withdrawal opening. The drive mechanism comprises:

(a) a means for moving the transfer pin along a first axis towards and away from the straw withdrawal opening, in which the tip portion engages a straw disposed in the straw withdrawal opening when the transfer pin is moved towards the straw withdrawal opening;

(b) means for rotating the transfer pin and straw in an assembled condition to a vertical orientation above the receptacle; and (c) means for lowering the transfer pin and straw such that the straw is placed into contact with the liquid in the receptacle and for raising the transfer pin so as to withdraw fluid from the receptacle. When the straw is lowered into the receptacle and vacuum is applied to the transfer pin, fluid is drawn into the straw. When the straw is raised out of the fluid, the straw removes the fluid from the receptacle.

Preferably, the housing for the straws comprises a cylindrical housing having an opening defining the straw withdrawal slot, and a concentric rotatable drum is placed within the cylindrical housing. The rotatable drum has a plurality of fingers and a motor for rotating the drum to sweep straws within the cylindrical housing, to provide a single straw into the straw withdrawal slot. A horizontal slide is disposed adjacent to and below the slot. The slide is movable from a first position away from the slot enabling straws to be withdrawn from the housing, to a second position obstructing the slot and preventing the straws from being withdrawn from the straw withdrawal slot.

BRIEF DESCRIPTION OF THE DRAWINGS

In the following detailed description, a presently preferred embodiment of the invention is described in conjunction with the appended drawings, wherein like reference numerals refer to like elements in the various views, and wherein.

DETAILED DESCRIPTION OF THE PREFERRED EMBODIMENT OF THE INVENTION

Overview of Preferred Sample Testing Machine

Figure 1:
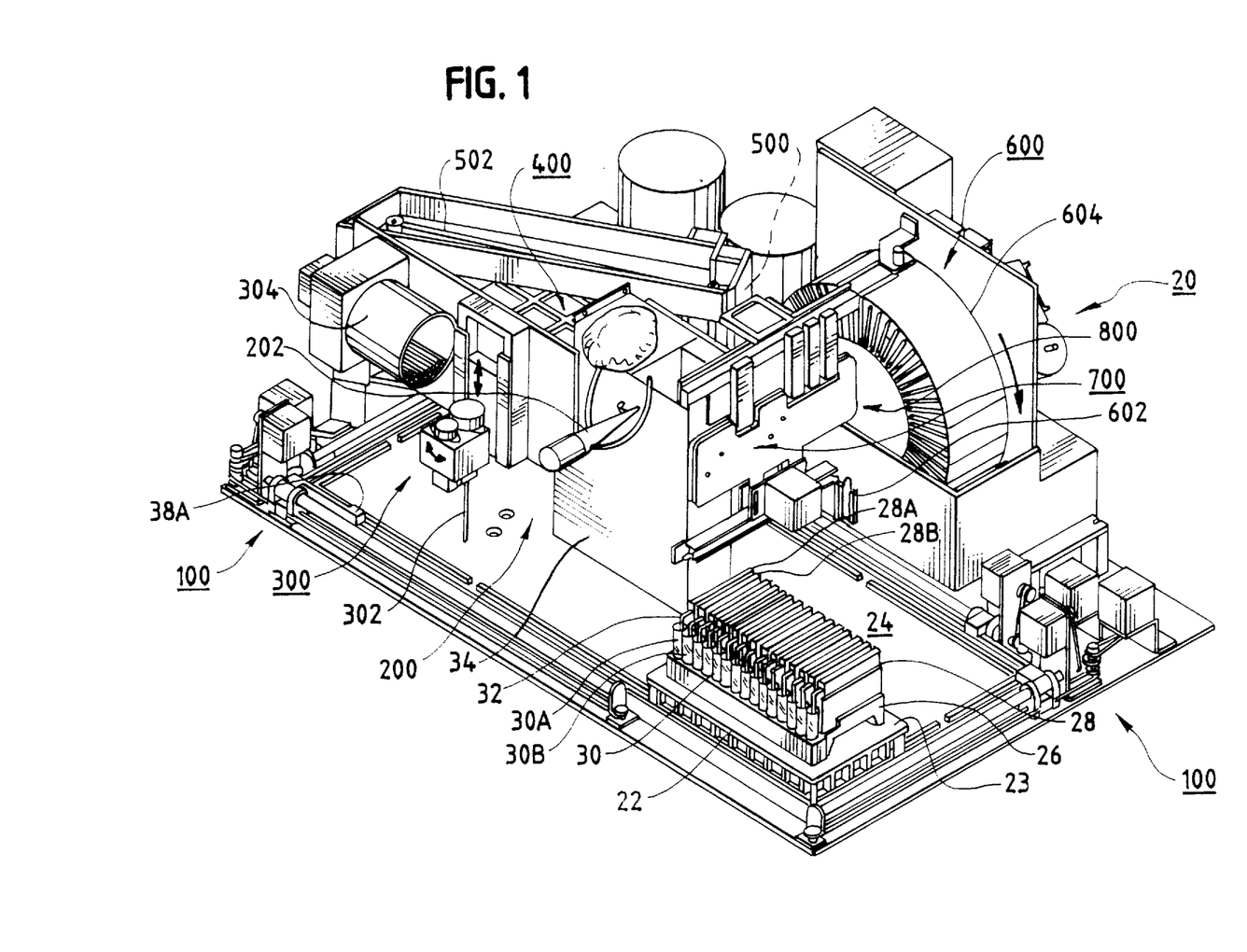
FIG. 1 is a perspective view of a preferred automatic biological sample testing machine that incorporates the diluting and pipetting stations of the present invention.

FIG. 1 is a perspective view of a preferred biological sample testing machine 20. The following detailed description of the preferred embodiment of the diluting and pipetting invention will be discussed in the context of the biological sample testing machine 20. It will be appreciated, however, that the invention may be used in other types of automatic testing machines besides the preferred biological sample testing machine 20. Other possible implementations include chemical testing, immunochemistry, immunodiagnostic, and nucleic acid probe assay machines.

The biological sample testing machine 20 includes a biological test sample positioning system 100, consisting of four independent motor-driven paddles, which is designed to slide a sample tray 22 (referred to herein as a "boat") across a base pan 24 around the machine 20 to several discrete stations, where various operations are performed on the samples in the boat 22. Prior to the start of the procedure, a technician loads a cassette 26 with a plurality of test cards 28 and receptacles such as test tubes 30 containing biological or control samples to be tested. Each test card 28 has an L-shaped transfer tube 32 protruding therefrom for permitting the fluids containing biological samples to be drawn from the test tubes 30 into the wells of the test cards 28. The technician places the loaded cassette 26 into the boat 22 at a loading station for the machine, such as the front, right hand corner of the base pan 24 shown in FIG. 1. The combined boat 22 and loaded cassette 26 are then moved as a unit over the surface of the base pan 24 about the machine 20 by the test sample positioning system 100.

In a typical microbiological testing scenario, described below for purposes of illustration but not limitation, the test cards 28 come in two varieties: (1) identification cards, in which particular different growth media are placed in the wells of the card 28 when the cards are manufactured, and (2) susceptibility cards, in which different concentrations of different antibiotics are placed in the wells of the card 28. The identification cards are used to identify the particular unknown biological agent, i.e., microorganism, present in the sample. The susceptibility cards are used to determine the susceptibility of the biological agent to various concentrations of antibiotics or other drugs. In the test procedure described below, identification and susceptibility tests can be performed on a single sample in one cycle of operation of the machine 20. To accomplish this, the cassette 26 is loaded such that a test tube 30A containing a biological sample, connected via a transfer tube 32 to an identification card 28A, is placed adjacent to a test tube 30B connected via a transfer tube 32 to a susceptibility card 28B.

The cards 28 preferably contain bar codes as well as other identifying indicia across the top of the card for reading by a bar code reader built into the machine 20. The bar codes are unique to each card, and identify card information such as card type, expiration date, and serial number, and are used to correlate test data and/or results from the cards with the patient and the biological sample. In addition, the entire boat or cassette may have sample information for all of the cards loaded in the cassette stored on a memory device affixed to the cassette 26, such as a memory button or "touch button" available from Dallas Semiconductor Corp., 4401 S. Beltwood Parkway, Dallas Tex.

In the representative example shown in FIG. 1, seven or eight of the test tubes 30 in the boat 22 contain biological samples, and are in fluid communication with identification cards 28A by the straw-like transfer tube 32. The biological sample test tube 30A and its associated identification card 28A can be thought of as a set. The biological sample test tubes and identification cards are typically arranged in an alternating pattern in the cassette 26. Each biological sample test tube 30A and identification card 28A set is adjacent to an empty test tube 30B placed in communication with a susceptibility card 28B via a transfer tube 32. It will be appreciated that the cards and associated test tubes could be ordered in any order in the cassette 26 depending on the particular testing requirements for the samples. For example, the cards could be arranged as follows: identification (ID), susceptibility (SU), ID, ID, ID, SU, SU, ID, SU . . . . Further examples would be all identification cards and all susceptibility cards.

The test sample positioning system 100 operates to move the boat 22 and cassette 26 over the base pan 24 first to a diluting station 200. The diluting station contains a rotating shot tube 202, by which a predetermined volume of diluent (such as saline solution) is added to the empty susceptibility test tubes in the cassette 26, e.g. test tube 30B. As the leading edge of the boat 22 is moved to the left during this process, it passes under a pipetting station 300. The pipetting station 300 includes a mechanism that automatically removes a pipette 302 from a source of pipettes 304, lowers the pipette 302 into the biological sample test tube 30A, and removes with vacuum a predetermined volume of biological fluid from the biological sample test tube 30A using the pipette 302.

The test sample positioning system 100 then moves the boat 22 to the left by an amount equal to the separation distance between adjacent test tubes 30A and 30B, e.g. 15 mm. The pipetting station 300 then lowers the pipette 302 containing the biological fluid from the biological sample test tube 30A into the adjacent susceptibility test tube 30B (having already received a quantity of diluent from the diluting station 200), expels the fluid into the test tube 30B, and drops the pipette 302 into the susceptibility test tube 30B. The process of movement of the boat 22 by the test sample positioning system 100, adding diluent to the susceptibility test tubes 30B at the diluting station 200, and transferring of biological samples from the biological sample test tubes 30A to the adjacent susceptibility test tubes 30B at the pipetting station 300, continues until all of the identification and/or susceptibility test tubes sets (if any) in the boat 22 have been so processed. By virtue of the close spacing of the pipetting station 300 and the diluting station 200, simultaneous diluting and pipetting operations can be performed on multiple test tubes in a single boat 22. After the last pipetting operation has been performed, the test sample positioning system 100 then moves the boat all the way to the left-hand edge of the base pan 24.

It will be understood by persons skilled in the art that the cassette 26 may be loaded entirely with biological samples in the test tubes 30 and identification cards 28, such as the case where a batch of biological samples are to be tested to identify the contents of the samples. In this example, the diluting and pipetting operations are not necessary. However, in other types of sample testing, other diluents or fluids may be added to or withdrawn from the test tubes. In the example of where no diluting or pipetting operations are performed (e.g., where the pipetting and diluting operations were performed off-line), the cassette 26 is loaded with test tubes and cards, and the positioning system 100 would simply move the boat 22 and loaded cassette 26 directly past the diluting station 200 and the pipetting station 300 without stopping, all the way to the left hand edge of the base pan 24.

Once at the left hand edge of the base pan 24, the test sample positioning system 100 operates to move the boat 22 along the left hand edge to a vacuum station 400. The vacuum station 400 is seen better in FIG. 2, which is a perspective view of the machine 22 with the diluting station 200 and the pipetting station 300 removed. At the vacuum station 400, a vacuum chamber 402 is lowered onto the boat 22 such that the bottom surface of the vacuum chamber 402 sealingly engages the top peripheral surface 23 of the boat 22. Vacuum is applied to the chamber 402 under microprocessor control, causing air in the interior of the test sample cards 28 to evacuate out of their associated test tubes and to be withdrawn from the chamber 402. The vacuum cycle is precisely managed to optimize filling using a closed loop servo system to regulate the change of vacuum and timing of the complete cycle. After a predetermined period, the chamber 402 is vented to atmosphere under microprocessor control. The venting of the cards causes the fluid in the test tubes 30 to be drawn into the cards 28, filling the wells in the cards 28.

Figure 2:
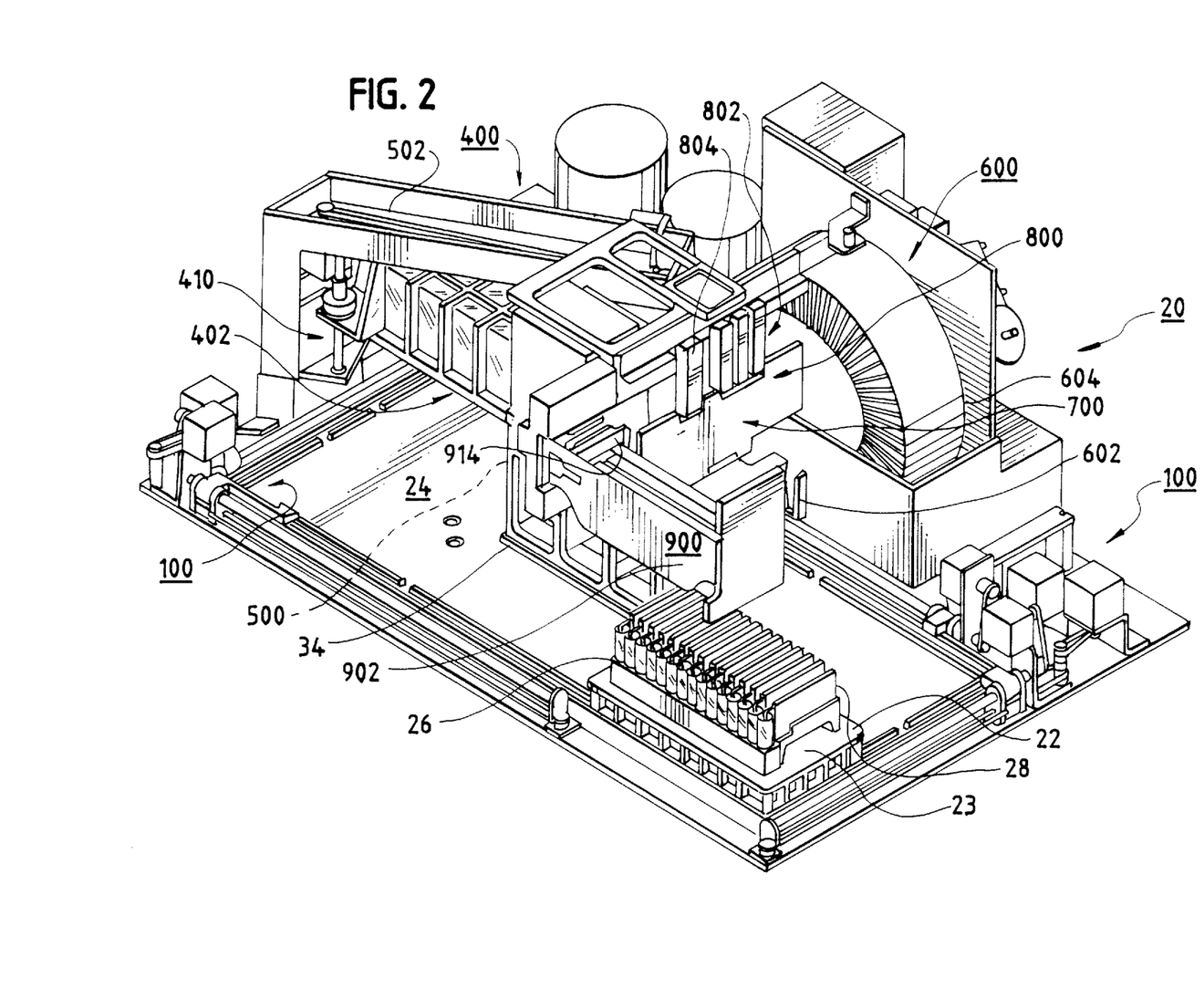
FIG. 2 is a perspective view of the machine of FIG. 1, with the diluting and pipetting stations removed to better illustrate the vacuum station of the machine.

The test sample positioning system 100 then operates to advance the boat 22 to the right across the rear of the base pan 24 to a cut and seal station 500, located behind the center mount 34 in FIGS. 1 and 2. The cut and seal station 500 consists of a hot cutting wire and attached support plate (not shown), and a drive mechanism 502 that lowers the cutting wire and support plate to the same elevation as the top portion of the transfer tubes 32 adjacent to where the transfer tubes 32 enter the test cards 28. As the boat 22 is advanced past the cut and seal station 500, the transfer tubes 32 are forced past the hot cutting wire. With the assistance of fore and aft constraints placed on the movement of the cards 28 by the walls of the cassette 26, and the lateral constraints on the movement of the card 28 by the cassette and wall structures of the machine 20, the hot cutting wire cuts the transfer tubes 32 by melting of the transfer tube material as the boat 22 is advanced past the hot cutting wire. A small stub of transfer tube material is left on the exterior of the card 28. The stub seals the interior of the card 28 from the atmosphere.

The test sample positioning system 100 then advances the boat 22 across the rear of the base pan 24 behind the center mount 34 to a carousel incubation station 600. A reciprocating cam driver is mounted to the center mount 34 opposite a slot 602 in the machine that pushes the cards off the cassette 26 one at a time through the slot 602 into a carousel 604. The carousel 604 is housed in an enclosure that is maintained at an appropriate incubation temperature for the particular assay, for example, 35 degrees C. The enclosure is partially broken away in FIGS. 1 and 2 in order to show the carousel 604. The carousel 604 is rotated in synchronism with the movement of the boat 22 over the rear of the base pan 26 by the test sample positioning system 100, so as to place the next slot in the carousel 604 in line with the slot 602 opposite the next card in the cassette 26. If the carousel is only going to be partially loaded with cards, it may be advisable to load the cards into every other slot a slot or two periodically in order to balance out the weight distribution in the carousel 604. For example, where the carousel has 60 slots and only 30 cards are to be processed, the cards are loaded into every other slot.

After all of the cards 28 have been loaded into the slots of the carousel 604, the boat 22 is advanced along the right hand edge of the base pan 24 back to its starting position (shown in FIGS. 1 and 2) or an exit position for removal of the cassette 26 (containing the test tubes and transfer tubes remnants) and receipt of a new cassette. Alternatively, the boat 22 could be moved to an exit station located, for example, in the rear or right hand side of the base pan 24.

As the cards 28 are being incubated in the incubation station 600, the cards are periodically, sequentially pushed out of the slots of the carousel 604 at the top of the carousel 604, one at a time, and moved by an optical scanner transport station 700 past a fluorescence and transmittance optics station 800. The wells of the card 28 are selectively subject to transmittance and/or fluorescence optical testing according to the analysis needed to be performed by the transmittance and fluorescence optics station 800. The transmittance and fluorescence optics station 800 includes detectors and processing circuitry to generate transmittance and fluorescence data for the wells in the cards 28, and to report the data to a central processing unit for the machine 22. If the test is not complete, the transport station 700 moves the card 28 back into its slot in the carousel 604 for more incubation and additional reading.

Typically, each card will be read every 15 minutes as the carousel makes one revolution. Typical incubation times for the cards 28 are on the order of two to eighteen hours, consisting of roughly four transmittance and fluorescence data sets per hour for each of the wells in the card 28 subject to the optical analysis requirements.

After the testing is complete, the cards are moved by the optical scanner transport system 700 into a card output station 900 shown in FIG. 2. The card output station 900 consists of a detachable tray 902 that is placed to the side of the optical station 800 at approximately the same elevation as the optical station 800. The technician removes the tray from the machine 20 as needed or when the tray is full of cards, empties the cards into a suitable biohazard disposal unit, and replaces the tray 902 back into the machine 20.

Diluting Station 200

Figure 3:
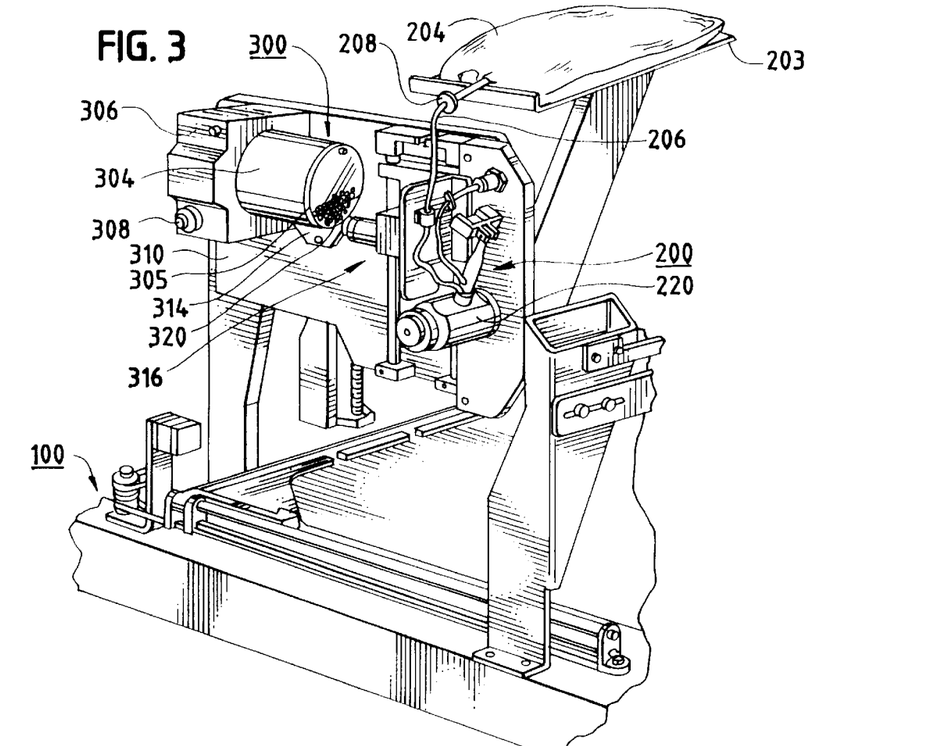
FIG. 3 is a more detailed perspective view of the diluting and pipetting stations of FIG. 1.
Figure 4:
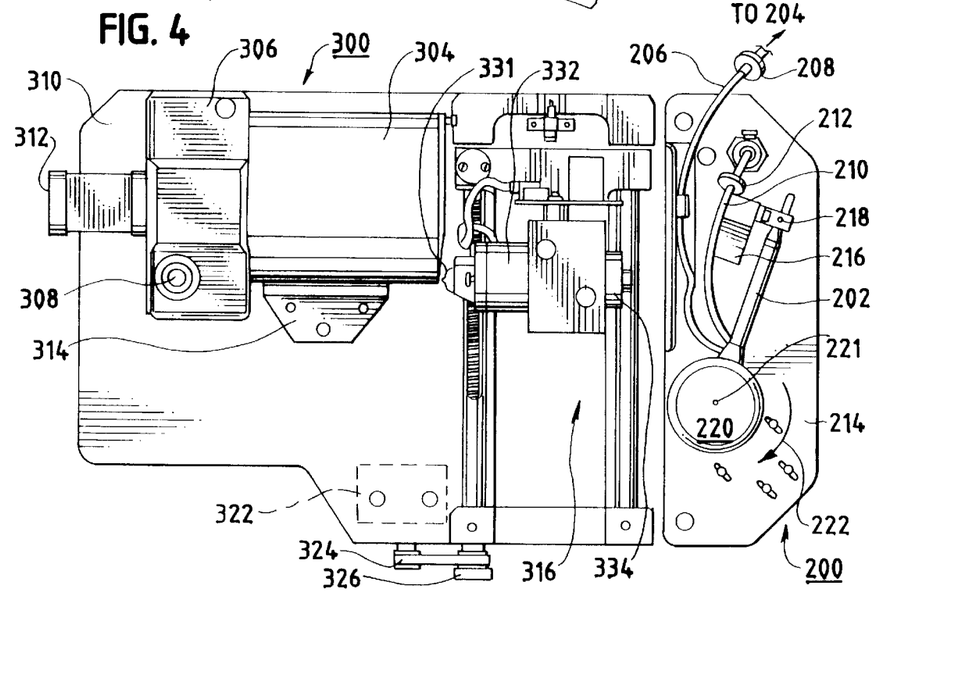
FIG. 4 is an elevational view of the diluting and pipetting stations of FIGS. 1 and 3.
Figure 5A:
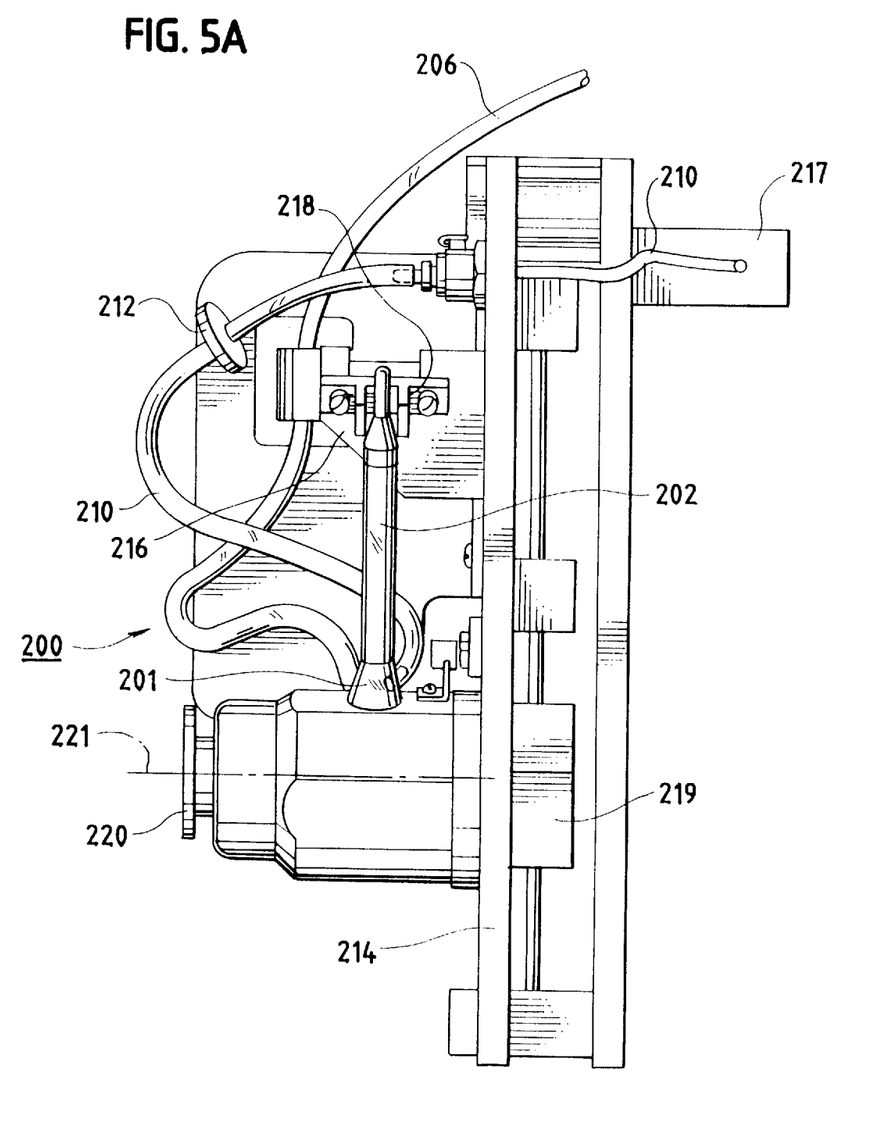
FIG. 5A is a side view of the diluting station of FIG. 3.

The diluting station of FIG. 1 is shown in more detail in FIGS. 3, 4 and 5. FIG. 3 is perspective view of the diluting and pipetting stations 200 and 300, respectively. FIG. 4 is an elevational view of the stations, and FIG. 5A is a side elevational view of the diluting station 200.

Referring to FIGS. 3–5A, the diluting station 200 can be thought of as a system for dispensing a controlled volume of fluid into a receptacle such as a test tube. The station 200 has a source of diluent fluid 204, such as a flexible bag of saline solution, that rests on a suitable inclined shelf 203. A rotating shot tube 202 having a predetermined volume receives the fluid from the source 204 via a conduit or tube 206. A filter 208 is placed in the conduit 206, and serves to prevent contaminants from entering the line 206.

A solenoid 220 is provided for controlling the opening of a thimble valve placed within the open end 201 of the shot tube 202. The thimble valve controls the flow of the fluid from the conduit 206 into the shot tube 202. Since the source of fluids 204 is placed above the shot tube 202, the fluid fills the shot tube 202 by gravity flow. The shot tube 202 is mounted to the solenoid 220 housing. The solenoid 220 and attached shot tube is rotatable via a motor 219 (FIG. 5A) having a drive belt and pulley (not shown) relative to a bulkhead 214. The motor 219 is placed directly behind the solenoid 202 on the back side of the bulkhead 214.

When the shot tube 202 is rotated to a generally upward orientation (i.e., the tip of the shot tube is elevated with respect to the end 201 of the shot tube), such as that shown in FIGS. 1, 3 and 4, the shot tube can be filled with fluid such that the shot tube is automatically primed as it is filled. The upward orientation of the shot tube 202 permits air within the shot tube to be eliminated from the shot tube 202 as the fluid enters the end 201 of the shot tube and works its way up to the tip of the shot tube 202. An optical sensor 218 mounted to a bracket 216 is provided for detecting when the diluent fills the shot tube up to the fill zone adjacent to the tip of the shot tube 202.

When the shot tube is filled, the motor 219 behind the bulkhead 214 rotates the solenoid 220 and shot tube 202 in the direction of the arrow 222 (FIG. 4) to a second position, wherein the tip portion of the shot tube 202 is oriented downward towards a test tube in the boat 22 (FIG. 1). A second conduit 210 is provided which is in communication with a source of compressed air 217 mounted behind the bulkhead 214. A filter 212 is provided in the conduit 210, and prevents contaminants from entering the line 210. The conduit 210 is fitted over an exhaust tube in the shot tube 202 in the vicinity of the thimble valve. When the shot tube 202 is in the second downward position, compressed air is injected into the shot tube in a stream to exhaust the diluent from the shot tube 202 into the test tube 30B (FIG. 1).

Figure 5B:
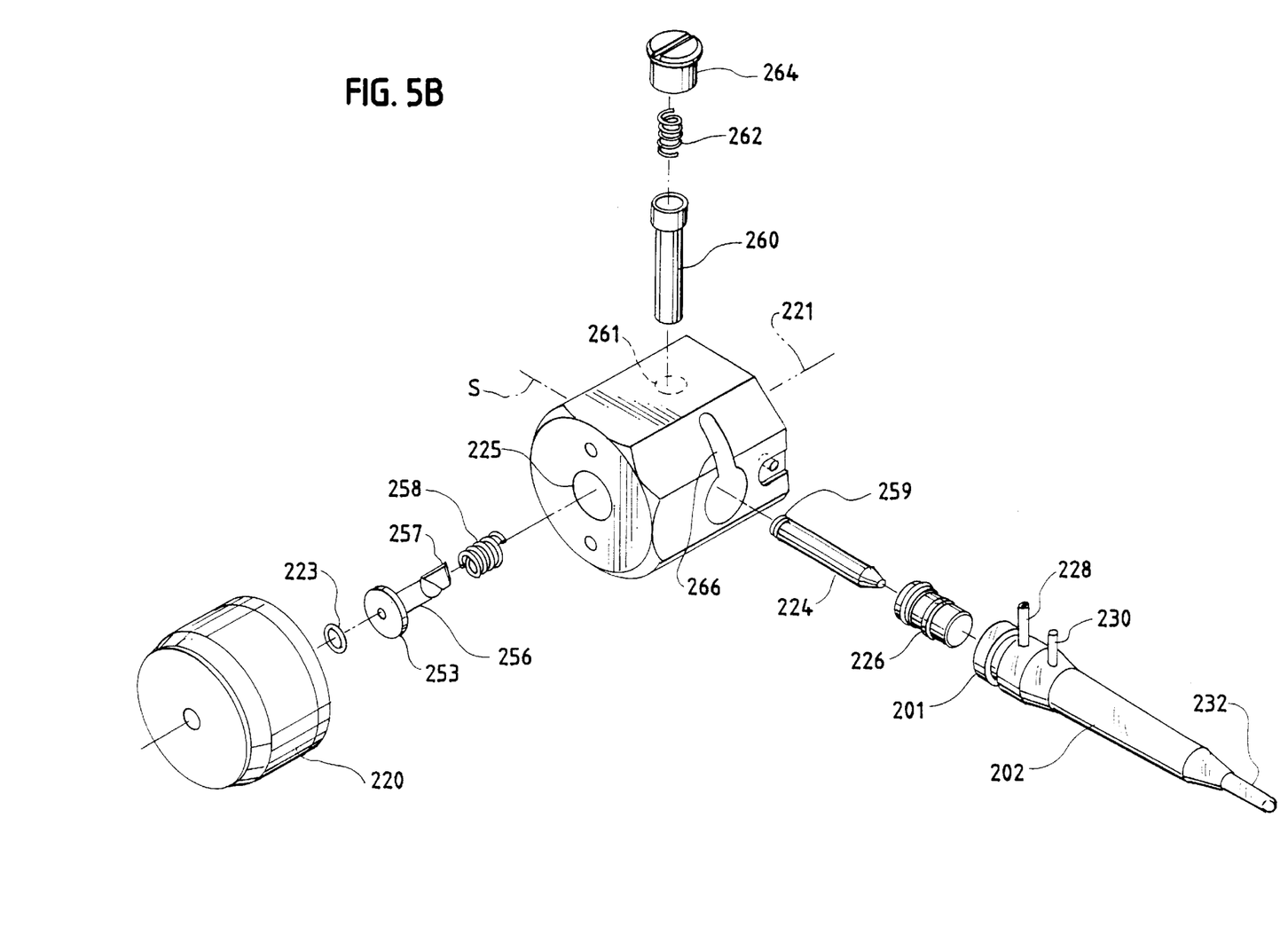
FIG. 5B is an exploded view of the solenoid and shot tube assembly of FIG. 5A.

Referring now to FIG. 5B, the solenoid 220 and shot tube 202 are shown in an exploded view. The solenoid 220, when energized, actuates a cam slide 256 placed within the aperture 225 along the solenoid axis 221. The solenoid 220 has a cam spring 258 that biases the cam slide 236 to a valve closed position, towards the left in FIG. 5B. A rubber O-ring 223 seats onto the head 253 of the cam slide 256. The cam slide 256 has a cam surface 258 which cooperates with a cam surface 259 on a plunger 224 so as to translate cam slide motion along axis 221 into orthogonal plunger 224 motion along the shot tube axis S. The plunger 224 is moved into and out of engagement with the thimble valve 226 as described below, and opens the valve 226 when the plunger is moved to an extended position by the cam slide 256. This arrangement permits the solenoid to be mounted at a right angle to the shot tube 202, decreasing the amount of space between the pipetting and diluting stations and enabling simultaneous pipetting and diluting operations to performed on different test tubes in the boat.

The solenoid assembly of FIG. 5B further includes a shot tube opening 266 that receives the shot tube 202 and thimble valve 226 when the shot tube 202 is in an assembled condition. The shot tube 202 has an exhaust tube 230 connected to the exhaust conduit 210 and a fill tube 228 connected to the diluent conduit 206 (see FIG. 5A). A release pin 260, a spring 262 and a release pin cap 264 are provided to permit the user to engage and disengage the shot tube 202 and thimble valve from the rest of the assembly, such as when the user replaces the saline bag 204 and shot tube 202. The release pin 260 mounts to the top of the housing 221 through an aperture and recessed region 261 in the housing 221. When the release pin 264 is rotated, the spring 262 lifts the release pin 264 out of engagement with the end 201 of the shot tube 202, permitting the shot tube 202 to be removed from the housing 221.

Figures 6, 7, 8:
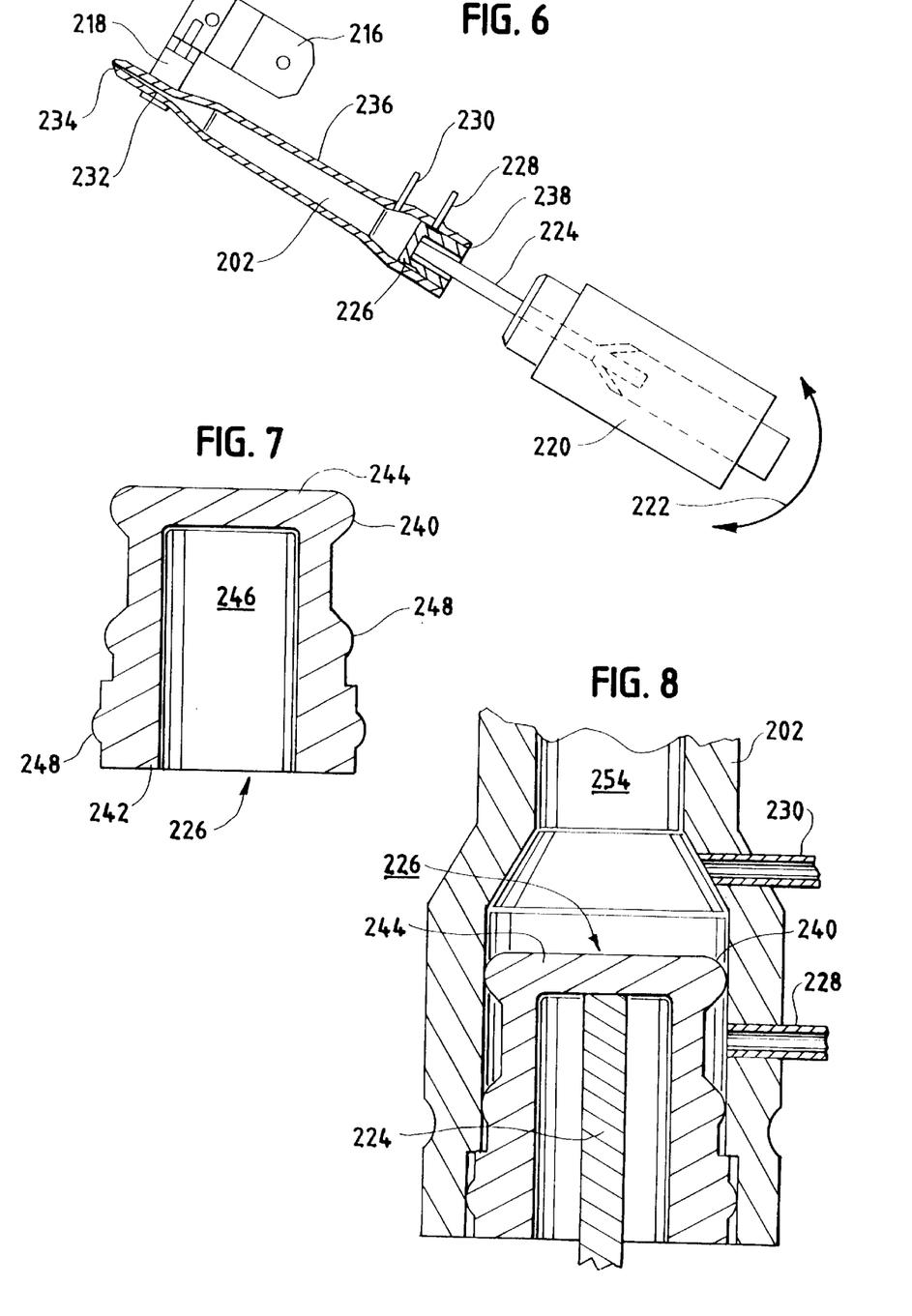
FIG. 6 is an isolated view of the diluting station of FIG. 3, partially in section, showing the shot tube and thimble valve in greater detail.
FIG. 7 is an isolated, sectional view of the thimble valve of FIG. 6.
FIG. 8 is an isolated, sectional view of the shot tube and thimble valve of FIG. 6, showing the relationship of the plunger relative to the thimble valve when the valve is in a closed condition relative to the fluid intake port.

Referring now to FIG. 6, the shot tube 202, solenoid 220 and optical sensor 218 are show isolated from the machine 20, with the shot tube 202 and thimble valve 226 shown in section. The solenoid 220 includes a valve plunger 224 that is disposed within the interior of the thimble valve 226. Referring to FIG. 7, the thimble valve 226 is shown isolated in a sectional view. The thimble valve 226 is a thimble-shaped member made of a resilient material such as silicone. The valve 226 has a wall portion 244 and a front sealing rib 240 that sealingly engages the interior of the shot tube in a compression seal to seal off the fill tube 228 connected to the source 204 of diluent. The thimble valve 226 has an annular body portion 242 that defines rear sealing ribs 248 that fit into complementary recessed regions in the interior of the shot tube 202 adjacent to the end 201 of the shot tube 202, and constrain the thimble valve 226 in the open end 201 of the shot tube 202. The body portion 242 defines a central chamber 246 for receiving the plunger 224.

Figure 9:
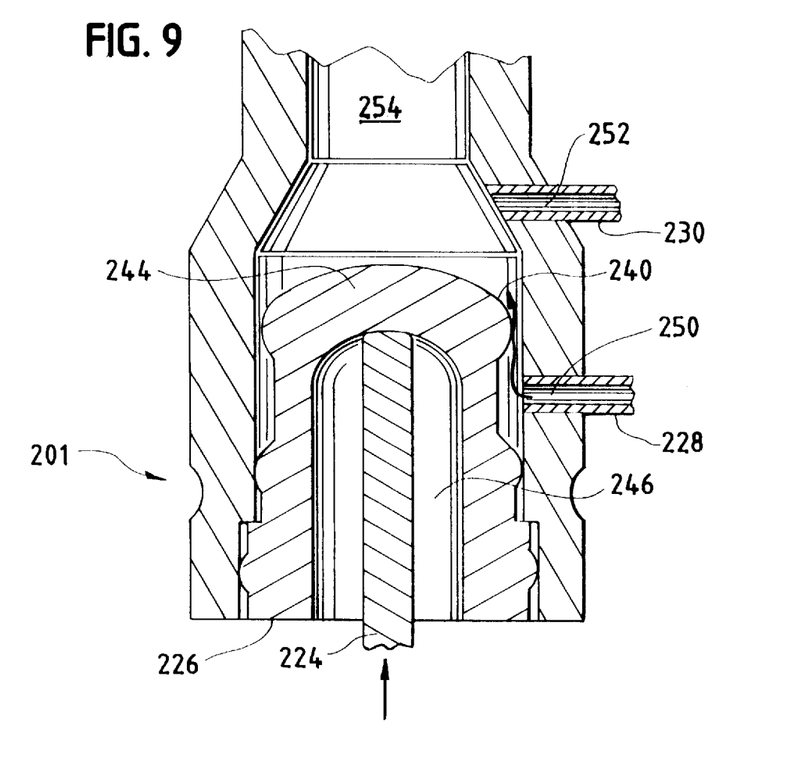
FIG. 9 is an isolated, sectional view of the shot tube and thimble valve of FIG. 6, showing the relationship of the plunger relative to the thimble valve when the valve is in an open condition relative to the fluid intake port.

FIG. 8 shows the position of the plunger 224, thimble valve 226, fill tube 228 and shot tube 202 when the thimble valve 226 is in a closed condition. The front sealing rib 240 seals off the fill tube 228, preventing fluid from entering the interior region or chamber 254 of the shot tube 202. FIG. 9 shows the position of the plunger 224 and thimble valve 226 when the plunger 224 is pushed by the solenoid 220 against the wall 244 to an extended position. The plunger 224 pushes against the wall 244 to extend and stretch the thimble valve 226 in a manner to cause the front sealing rib 240 to move away from the interior surface of the shot tube 202 towards the interior 254 of the shot tube 202, permitting fluid to flow from the fill tube port 250 around and past the rib 240 into the interior 254 of the shot tube 202.

Referring to FIGS. 6 and 9, when the tube 202 is filled with diluent up to the shot tube optical sensor zone 232, the plunger 224 retracts to the position shown in FIG. 8, shutting off the flow of fluid. Preferably, the optical sensor fill zone 232 is given a tapered shape as shown so as to define a small volume for the diluent, permitting filling of the shot tube with precision. The tapered optical sensor fill zone 232 and resulting small volume allows only a very small volume of fluid to travel beyond the optical sensor 218 during the closing of the thimble valve 336. The shot tube 202 is then rotated to a downward vertical position above the susceptibility test tube, whereupon compressed air is supplied via conduit 210 and exhaust tube 230 to an exhaust port 252 and into the interior of the shot tube 202. The stream of compressed air forces the fluid in the interior region out the tip 234 of the shot tube 202.

From FIGS. 8 and 9, it can be seen that in its relaxed, normal position, the thimble valve 226 is closed. The retraction of the plunger 224 from the wall 244 of the thimble valve 226 to close the valve helps prevent any pressure surges or "water hammer" effect to be generated in the filled shot tube 202, as would be the case if the thimble valve were to be designed to be pushed to an extended position to close the port 250. If pressure surges were to cause diluent to eject out of the tip 234 of the shot tube 202, contamination of the shot tube could potentially result. Hence, a design of a thimble valve 226 that is retracted to close the valve, preventing pressure surges, is a preferred design.

In a preferred form of the invention, the saline bag 204, conduit 206 and shot tube 202 are combined and installed in the machine 20 as a replaceable, disposable fluid delivery unit. When the saline bag 204 is empty, the user simply replaces the saline bag 204, shot tube 202 (including thimble valve 226) and conduit 206 as a single unit, avoiding any problems with contamination or disinfection of the shot tube 202. The conduit 210 may or may not be part of the fluid delivery unit, and, if not, it would fit over the exhaust tube 230 when the shot tube 202 and saline bag 204 are mounted in the machine 22.

Referring again to FIGS. 3 and 4, in a preferred embodiment the solenoid 220 is oriented relative to the shot tube 202 in a manner to save space and allow the shot tube 202 and solenoid 220 to be placed as close as possible to the pipetting station 300. The axis of the shot tube is perpendicular to the axis of movement 221 of the solenoid (into the page in FIG. 4). The cam slide 256 in the solenoid 220 translates motion in the direction of the axis 221 into plunger motion in the direction of the thimble valve and shot tube 202 along the axis S of the shot tube 202. This is shown in FIG. 5B.

Pipetting Station 300

The pipetting station 300 is shown in FIGS. 3 and 4 in an overall aspect. The station 300 includes a pipette hopper 304 and dispensing assembly shown in an end view in FIG. 11A and an exploded view in FIG. 12.

Figure 10:
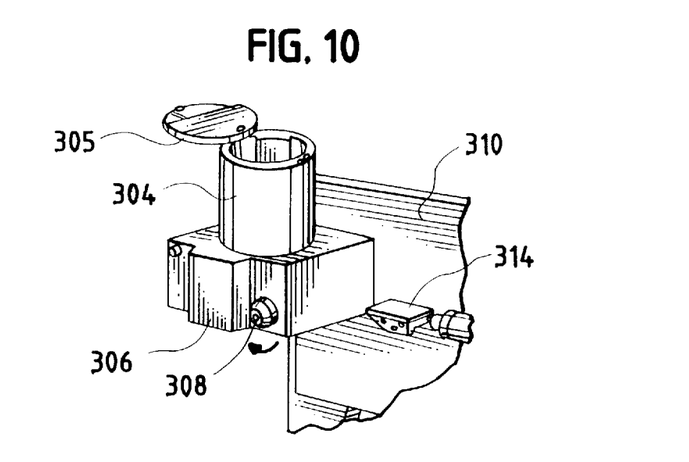
FIG. 10 is a perspective view of the pipetting hopper system of FIG. 3 when the pipette housing is rotated to a pipetting fill position, with the cover swung open to permit the housing to be filled with pipettes.
Figure 11A:
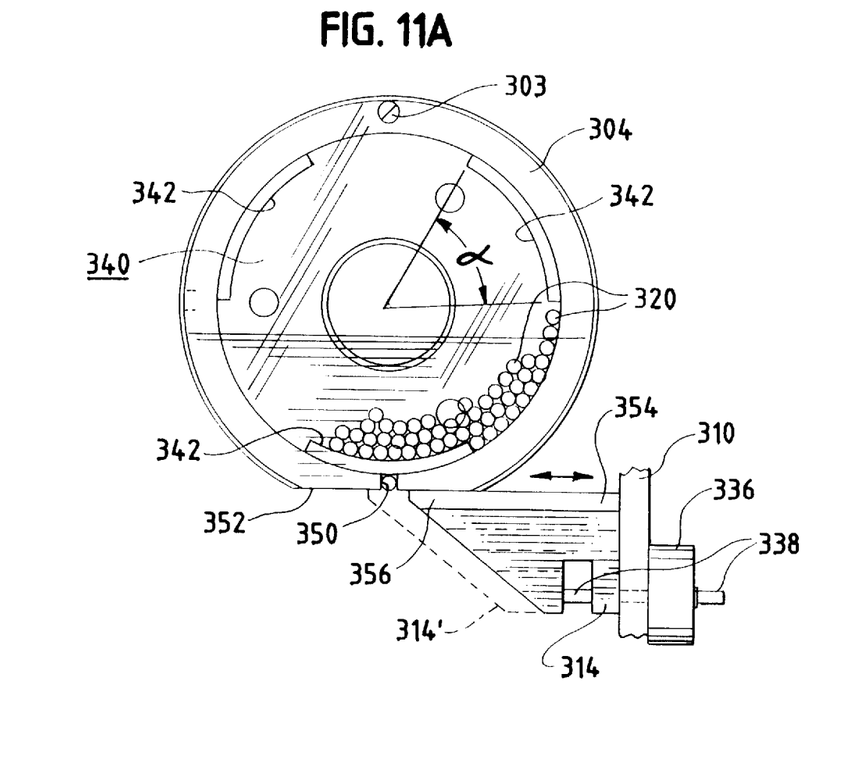
FIG. 11A is an end view of the pipetting hopper system showing the movement of a horizontal slide between two positions, controlling the ability of pipettes to be removed from the housing via a slot in the housing.
Figure 12:
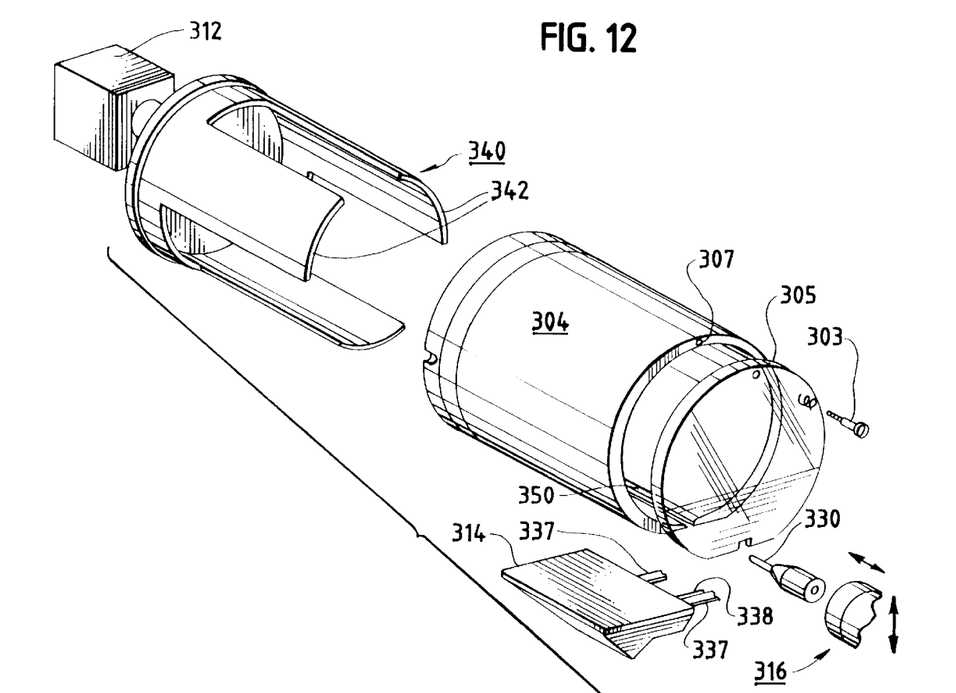
FIG. 12 is an exploded view of the pipette hopper system of FIGS. 3, 10 and 11.

Referring to FIGS. 3, 4, 10, 11A and 12 in particular, the station 300 includes a generally cylindrical housing or hopper 304 that contains a plurality of hollow pipette straws 320. As seen in FIG. 12, the housing 304 defines a horizontally disposed straw withdrawal opening slot 350 at the bottom of the housing 304. The housing 304 is mounted to a block 306 which is rotatable relative to a bulkhead 310 by a pin 308 secured to the bulkhead 310, so as to permit the housing 304 to rotate upwards from the orientation shown in FIG. 1 to the orientation shown in FIG. 10. The housing includes a clear plastic cover 305 which prevents the straws 320 from falling out of the housing 304. The plastic cover 305 is mounted to the housing 304 via a screw 303 and a mounting hole 307 (FIG. 12) in the housing 304. As shown in FIG. 10, the plastic cover 305 swings out from a position covering the housing 304 opening so as to permit a technician to refill the housing 304 with straws 320.

When the housing 304 is in the normal, horizontal position in FIGS. 1 and 11A, the slot 350 is positioned immediately above a horizontal slide member 314. Referring to FIG. 11A and 12, the horizontal slide 314 has a solenoid 336 that is mounted to the back side of the bulkhead 310 for moving the slide between extended and retracted positions. The solenoid 336 could be mounted to the front of the bulkhead in a different configuration if desired. The movement of the slide 314 is accomplished by moving a shaft 338 that the slide 314 is mounted to back and forth. The slide 314 is slid along guides 337.

Figure 11B:
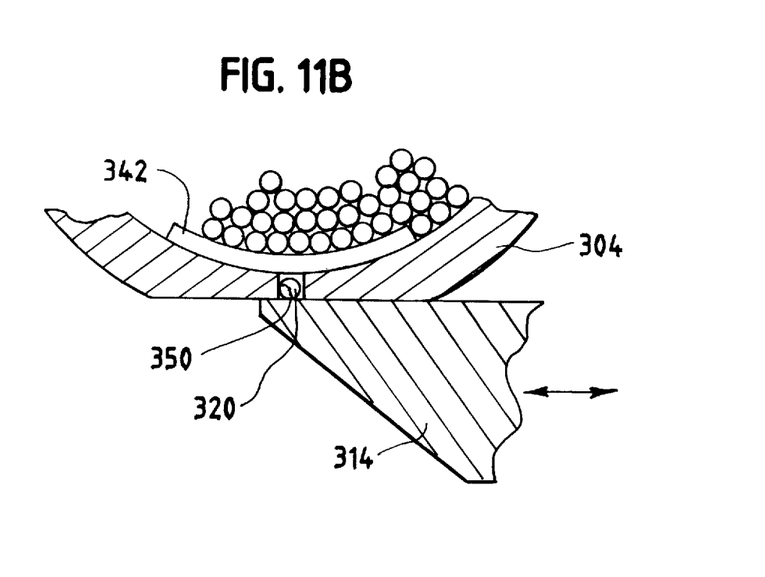
FIG. 11B is a sectional view of the slot of FIG. 11, showing the position of the fingers above the slot and the slide below the slot, firmly securing the straw in the slot.

A stepping motor 312 (FIGS. 4 and 12) mounted to the rear wall of the drum 340 is provided to sweep a rotatable drum 340 having three equidistantly spaced fingers 342 about the interior surface of the housing 304. In a preferred embodiment, each of the fingers 340 define a sweep angle α of approximately 60 degrees. As best seen in FIG. 11A, as the fingers 342 sweep along the interior surface of the housing 304, one of the fingers sweeps a straw 320 in the housing 304 into the slot 350. The fingers 342 stop their movement such that a portion of the finger 342 covers the slot 350, with a straw positioned below the finger in the slot, as shown in FIG. 11B. When the horizontal slide 314 is in the position 314' shown in dashed lines in FIG. 11A, the top surface 354 of the end portion 356 of the slide 314 is positioned below the slot 350 in contact with a bottom housing surface 352, preventing a straw 320 from falling out of the housing 304 through the slot 350. As shown best in FIG. 11B, the sides of the slot 350, the finger 342 and the slide 314 all cooperate to firmly retain the straw 320 in the slot, permitting the tapered tubular transfer pin 330 to be inserted into the end of the straw 320.

Figure 12A:
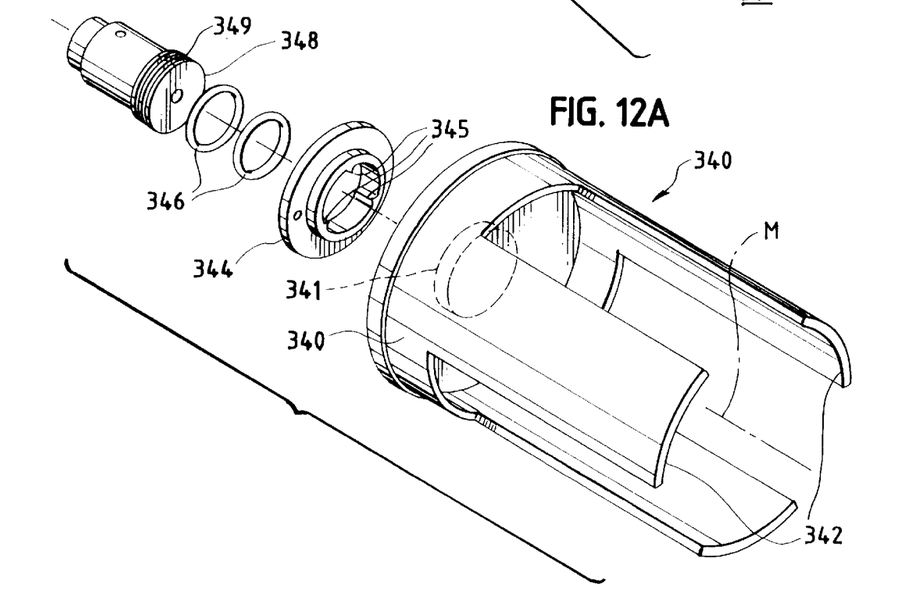
FIG. 12A is a more detailed exploded view of the rotatable drum of FIG. 12, showing the couplings that couple the motor 312 to the drum 340.

Referring to FIG. 12, the housing 304 is made from a low friction material such as DELBIN®. Preferably, the housing 304 is constructed such that the inside diameter of the housing 304 is less than the length of the housing, so as to maintain the straws 320 in a condition oriented parallel to the length of the housing 304, so that they can be readily swept into the slot 350. Referring now in particular to FIG. 12A, the drum 340 is shown in greater detail. A drive lug 348 is rotated by the motor 312 of FIG. 12. The drive lug 348 has pair of circumferential recesses 349. A pair of drive O-rings 346 fit over the recesses 349. The drive lug 349 fits into a grip sleeve 344 by means of a set of three inwardly projecting points 345, which securely grip the O-rings 346. The slip ring 344 in turn is securely mounted to the central aperture 341 in the rear wall of the drum 340. When the lug 348 is rotated by the motor 312, the drum 340 is rotated about the motor and drum axis M. The grip sleeve and O-ring construction of FIG. 12A reduces noise and vibration.

While the slide 314 is in the extended position 314' and the straw is trapped in the slot 350 as shown in FIG. 11 B, a tapered tubular transfer pin 330 (FIG. 4) is moved from a retracted position in a transfer pin assembly 316 into an extended position directly into the straw 320 in the slot 350, so as to frictionally engage the tip of the straw 320. The frictional engagement of the tubular transfer pin with the straw 320 is shown in detail in FIG. 13. At this point, the horizontal slide 314 retracts towards the bulkhead 310 (see FIG. 11A). The transfer pin 330 now is rotated by a motor 360 (FIGS. 14–16) to a vertical position as shown in FIG. 1, permitting the straw 320 to be moved through the slot 350 out of the housing 304. As soon as the straw 320 is rotated out of the slot 350, the slide 314 is moved back to the position 314' shown in dashed lines in FIG. 11A, and the motor 312 is operated to sweep another straw 320 into the slot 350.

The tapered tubular transfer pin 330 with attached straw 302, now in a vertical orientation directly above one of the test tubes in the cassette 26, is lowered so that the end of the straw 302 (FIG. 1) is immersed sufficiently into the fluid in one of the test tubes (e.g. test tube 30A), such as a test tube containing a biological or control fluid sample. Vacuum is applied to the tubular transfer pin 330 and attached straw 302 for a predetermined period of time, drawing a precise and controlled volume of fluid into the straw 302. The tubular transfer pin 330 and attached straw (with fluid) is raised up so as to clear the top of the test tube. The boat and test tube are advanced by the positioning system 100 by an amount equal to the separation distance of adjacent test tubes. The tubular transfer pin 330 and straw 302 are lowered into the susceptibility test tube 30B, whereupon the vacuum applied to the transfer pin 330 is released, causing the fluid contents of the straw 302 to fall into the susceptibility test tube 30B. At this point, the tubular transfer pin 330 is moved to a position wholly within the tubular transfer pin housing so as to eject the straw 302, dropping the straw in the susceptibility test tube. The transfer pin assembly 316 is then raised back to the elevation of the hopper 304, rotated into a horizontal position, and the process repeated.

Figure 14:
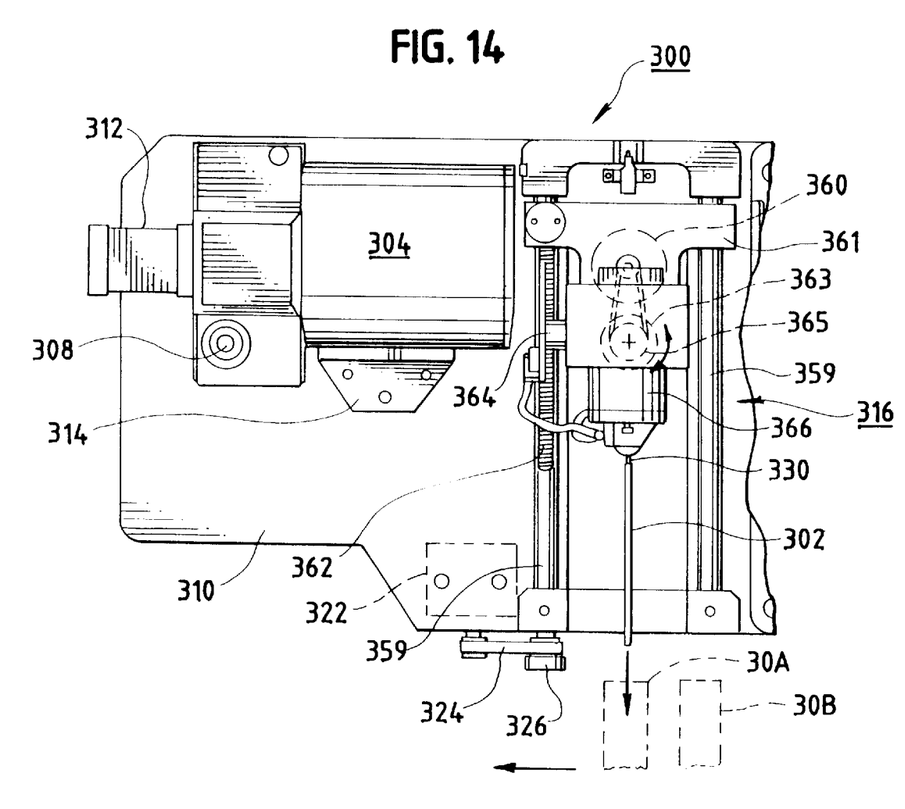
FIG. 14 is an elevational view of the pipetting station 300 with the tubular tapered transfer pin assembly rotated to fluid withdrawal position where the straw can be lowered into a receptacle.
Figure 15:
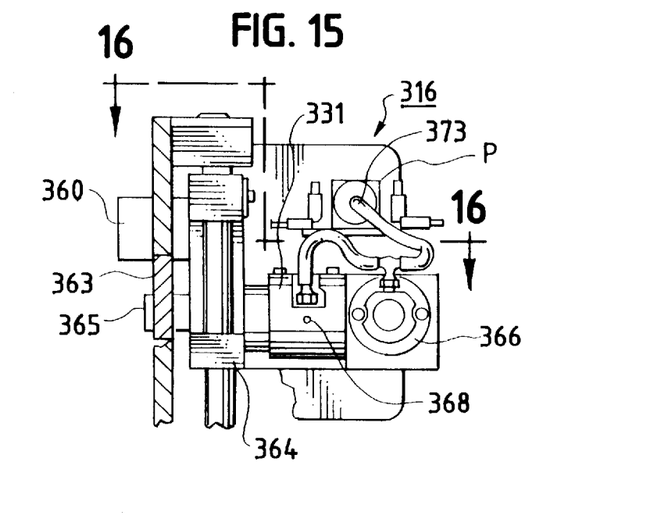
FIG. 15 is a side view of the tubular tapered transfer pin assembly as seen from the straw hopper 304 in FIG. 14.
Figure 16:
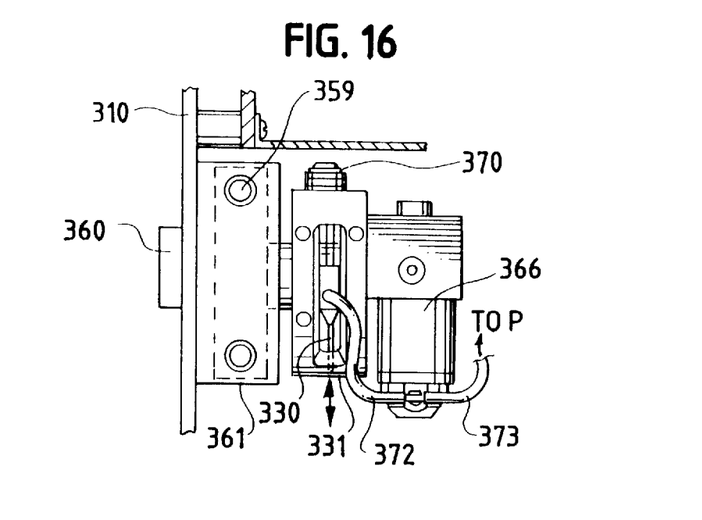
FIG. 16 is a top plan-view of the tubular tapered transfer pin assembly along the lines 16—16 of FIG. 15.

Referring to FIGS. 14, 15 and 16, the transfer pin assembly 316 and associated motor and vacuum system for the transfer pin 330 are illustrated in greater detail. Referring to FIG. 14 in particular, a motor 322 is mounted behind the bulkhead and includes a drive belt 324 that turns a pulley 326 and a threaded shaft 362, referred to in the art as an ACME thread or lead screw. A transfer pin plate 361 is mounted to the threaded shaft via a pair of collars 364. Depending on the direction that the motor 322 rotates the shaft 362, the plate 361 and attached transfer pin assembly 316 is slid either up or down the two pillars 359 between an upper position, in which the transfer pin 330 is at the same elevation as the straw withdrawal slot 350 in the housing 304, and a lower position in which the straw 302 is in a position to withdraw fluid from a receptacle placed below the transfer pin assembly 316.

A second motor 360 having a drive belt 363 and pulley 365 is mounted to the rear of the transfer pin plate 361, and is provided for rotation of the entire transfer pin assembly 316 in the direction of the arrow of FIG. 14 between a first position, in which the transfer pin 330 is oriented in the direction of the straw withdrawal slot 350, to a second position, in which the straw 302 is oriented vertically downward in the position shown in FIGS. 1 and 14.

Figure 13:
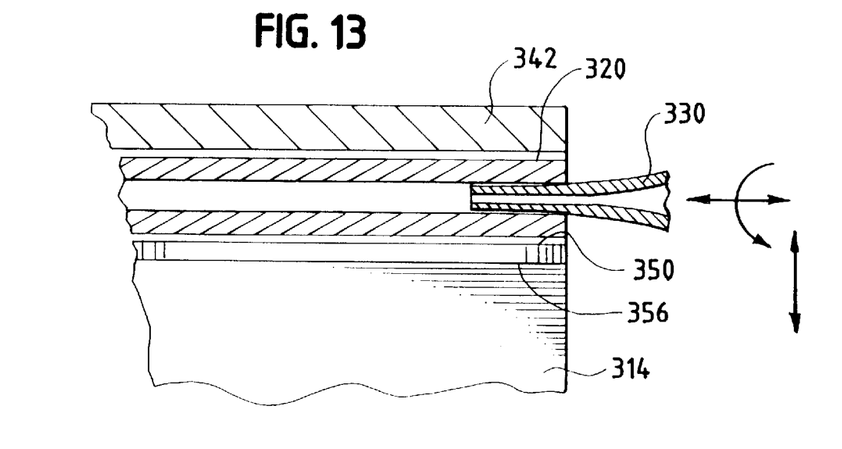
FIG. 13 is a detailed view, partially in section, of a portion of the pipette hopper system of FIG. 12, showing the insertion of the tapered tubular transfer pin into a pipette to make a friction fit with the pipette, permitting the pipette to be removed from the pipette housing.

Referring to FIG. 15, the transfer pin assembly 316 is illustrated in a side view as seen from the pipette housing 304. The transfer pin assembly has a transfer pin housing 331 which defines a transfer pin aperture 368. The tapered tubular transfer pin 330 (FIG. 16) reciprocates between a retracted position in the housing (shown in FIGS. 15 and 16), and an extended position shown in FIG. 14 at which it engages a straw in the straw withdrawal slot 350 as shown in FIG. 13. A transfer pin actuation solenoid 370 is mounted to the rear of the transfer pin assembly 316 to move the tubular tapered transfer pin 330 between the retracted and extended positions. A source of vacuum 366 is mounted adjacent to the transfer pin housing 331, and provides vacuum to the end of the transfer pin 330 via a tube 372. A vacuum pressure transducer P is provided which monitors the vacuum generated by the source 366 to ensure that a straw is attached to the tapered tubular transfer pin 330, that fluid is withdrawn into the straw, and that a sufficient volume of liquid is transferred. This pressure transducer P is positioned at the end of a secondary vacuum line 373 in communication with the vacuum source. A suitable pressure transducer P is the Motorola model MPX 5010D sensor.

When the transfer pin 330 and straw 302 are rotated from a horizontal position to the vertical position shown in FIG. 14, the straw 302 is rotated out of the slot 350 in the housing 304. The motor 322 then operates to lower the transfer pin assembly 316 to the appropriate level such that the straw 302 is immersed in the test tube 30A. After withdrawal of the fluid from the test tube 30A, the motor 322 raises the transfer pin assembly 316 up such that straw 302 clears the top of the test tube 30A, and then lowers the assembly 316 into test tube 30B after test tube 30B is placed below the straw 302. To remove the straw 302, the transfer tube 330 is retracted into the transfer tube housing 331. The diameter of the straw 302 is slightly larger than the diameter of the transfer pin aperture 368, forcing the straw 302 off of the transfer pin 330 as the transfer pin 330 with completely withdrawn into the transfer pin housing 331 in the position shown in FIG. 16. In this embodiment, the straw 302 falls into test tube 30B. The transfer pin assembly is then rotated back into a horizontal position and raised to the level of the straw withdrawal slot 350 in the housing 304, and the process is repeated for the next set of test tubes.

From the foregoing description, it will be appreciated that various modifications and alterations may be made to the preferred embodiment of the invention without departure from the true scope and spirit of the invention. For example, the pipetting and diluting stations may be used in other types of testing machines. The pipette withdrawal method described above may be used for other types of machines which need automatic withdrawals of straws. This true spirit and scope of the invention is defined by the appended claims, to be interpreted in light of the foregoing.

We claim:

1. A system for removing liquid from a receptacle, the system comprising:

an enclosure for a plurality of empty straws for use in said system comprising a housing containing a plurality of empty hollow straws and an opening defining a straw withdrawal slot, said enclosure further comprising a means for sweeping an empty straw in said housing into said straw withdrawal slot;

a tapered, tubular transfer pin having a tip portion;

a source of vacuum connected to said transfer pin;

a drive mechanism for said transfer pin, said drive mechanism comprising:

means for moving said transfer pin along a first axis towards and away from said straw withdrawal opening, said tip portion engaging a straw disposed in said straw withdrawal opening when said transfer pin is moved towards said straw withdrawal opening;

means for rotating said transfer pin and straw in an assembled condition to a vertical orientation, said vertical orientation above said receptacle when said receptacle is moved into a position below said system; and means for lowering said transfer pin and straw such that said straw is adapted to be placed into contact with said liquid in said receptacle and for raising said transfer pin so as to withdraw fluid from said receptacle when vacuum is applied to said transfer pin.

2. The system of claim 1, wherein said housing comprises a cylindrical housing for containing a plurality of said straws, said cylindrical housing having an opening defining a straw withdrawal slot, and wherein said system further comprises:

a concentric rotatable drum placed within said cylindrical housing, said rotatable drum comprising a plurality of fingers for sweeping straws within said cylindrical housing into said straw withdrawal slot; and a horizontal slide disposed adjacent said slot, said slide movable from a first position enabling said straws to be withdrawn from said cylindrical housing to a second position preventing said straws from being withdrawn from said straw withdrawal slot.

3. The system of claim 2, wherein said fingers comprise three fingers equidistantly spaced around said drum.

4. The system of claim 3, wherein each of said fingers define an angular sweep of approximately 60 degrees.

5. The system of claim 1, wherein said straws have a straw diameter and wherein said system further comprises a tapered pin housing having a pin aperture, wherein said tapered pin is movable relative to said tapered pin housing and pin aperture from extended and retracted positions, said pin housing having a diameter less than said straw diameter so as to cause said straw to become disengaged from said tapered pin upon retraction of said pin within said pin housing.

6. Apparatus for dispensing straws, comprising:

a cylindrical housing for containing a plurality of said straws, said cylindrical housing having an opening defining a straw withdrawal slot;

a concentric rotatable drum placed within said cylindrical housing, said rotatable drum comprising a plurality of inwardly disposed members for sweeping straws placed within said cylindrical housing into said straw withdrawal slot; and a slide disposed adjacent said slot, said slide movable from a first position enabling said straws to be withdrawn from said cylindrical housing to a second position preventing said straws from being withdrawn from said straw withdrawal slot.

7. The system of claim 6, wherein said housing defines an open end and a closed end, and wherein said system further comprises a clear cover covering said open end for maintaining said straws within said housing and permitting visual inspection of the quantity of straws within said housing.

8. The system of claim 7, wherein said cover is mounted to said housing to permit said cover to be rotated away from said open end to thereby permit said housing to be refilled with said straws.

9. The system of claim 6, wherein said inwardly disposed members comprise three fingers equidistantly spaced around said drum.

10. The system of claim 9, wherein each of said fingers define an angular sweep of approximately 60 degrees.

11. The system of claim 6, wherein said cylindrical housing defines a length of distance L and a diameter of distance D, and wherein D is less than L.

12. The system of claim 6, wherein said housing is made from a low friction material.

* * * * *